United States Patent [19]

Wickersheim et al.

[11] Patent Number: 4,785,824

[45] Date of Patent: * Nov. 22, 1988

[54] OPTICAL FIBER PROBE FOR MEASURING THE TEMPERATURE OF AN ULTRASONICALLY HEATED OBJECT

[75] Inventors: Kenneth A. Wickersheim, Menlo Park; Mei H. Sun, Los Altos, both of Calif.

[73] Assignee: Luxtron Corporation, Mountain View, Calif.

[*] Notice: The portion of the term of this patent subsequent to Dec. 2, 2003 has been disclaimed.

[21] Appl. No.: 65,316

[22] Filed: Jun. 22, 1987

[51] Int. Cl.⁴ .................... A61B 5/00; G01J 5/08; G01K 11/20; G01K 13/00
[52] U.S. Cl. .................... 128/736; 128/804; 374/131; 374/159; 374/161
[58] Field of Search .............. 128/736, 804; 374/130–131, 159, 161; 433/86

[56] References Cited

U.S. PATENT DOCUMENTS

| | | | |
|---|---|---|---|
| 4,016,761 | 4/1977 | Rozzell et al. | 374/161 |
| 4,136,566 | 1/1979 | Christensen | 374/161 |
| 4,140,393 | 2/1979 | Cetas | 356/43 |
| 4,223,226 | 9/1980 | Quick et al. | 250/458 |
| 4,245,507 | 1/1981 | Samulski | 356/44 |
| 4,316,388 | 2/1982 | Miller et al. | 374/161 |
| 4,376,890 | 3/1983 | Engstrom et al. | 250/277 |
| 4,397,314 | 8/1983 | Vaguine | 128/399 |
| 4,448,547 | 5/1984 | Wickersheim | 374/131 |
| 4,542,987 | 9/1985 | Hirschfield | 374/131 X |
| 4,562,348 | 12/1985 | Brogardh et al. | 374/130 X |
| 4,592,664 | 6/1986 | Bijlenga et al. | 374/131 |
| 4,626,110 | 12/1986 | Wickersheim et al. | 374/131 |
| 4,695,709 | 9/1987 | Sachs et al. | 128/736 X |

FOREIGN PATENT DOCUMENTS

WO87/02769 5/1987 PCT Int'l Appl. .

OTHER PUBLICATIONS

Wickersheim et al., Ultrasound-Immune Fiberoptic Thermometry Probe; 5/1985.

Primary Examiner—Edward M. Coven
Assistant Examiner—Angela D. Sykes
Attorney, Agent, or Firm—Majestic, Gallagher, Parsons & Siebert

[57] ABSTRACT

An optical fiber temperature sensing probe for implantation into a human body or other object that is being heated either by ultrasonic radiation alone or by a combination of ultrasonic and electromagnetic (radio frequency or microwave) energy. Several embodiments are described of probes adapted to measure temperature in an ultrasound field without errors being introduced by direct absorption of ultrasonic energy or by viscous heating, even when plastic fiber is utilized.

17 Claims, 1 Drawing Sheet

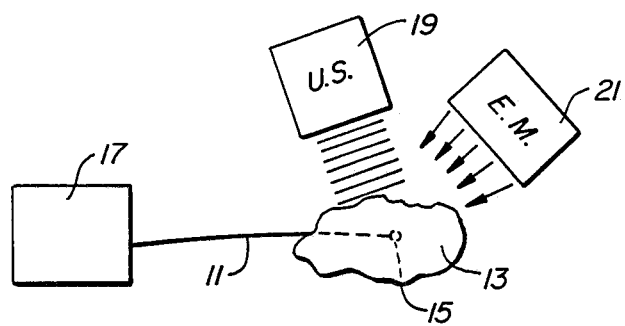
FIG._1.
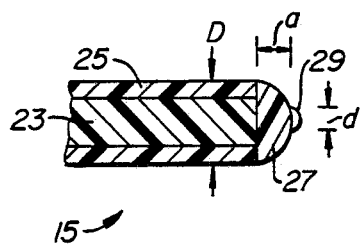
FIG._2.
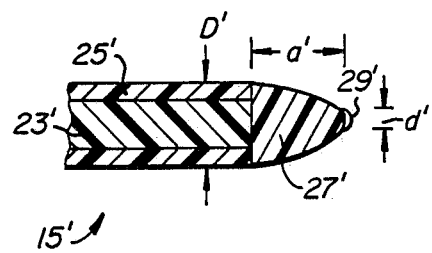
FIG._3.
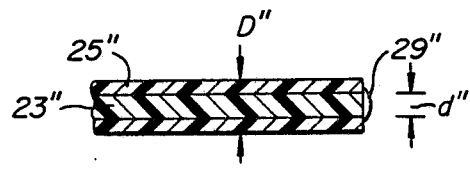
FIG._4.
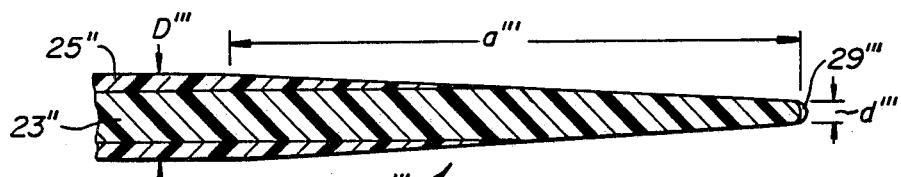
FIG._5.

OPTICAL FIBER PROBE FOR MEASURING THE TEMPERATURE OF AN ULTRASONICALLY HEATED OBJECT

BACKGROUND OF THE INVENTION

This invention relates generally to optical temperature sensing techniques, and more specifically to such techniques applied to measure the internal temperature of objects heated by electromagnetic radiation and/or ultrasonic energy.

There are many applications where the internal temperature of a fluid bath or more solid object is to be measured in an electromagnetic radiation and/or ultrasonic energy field that is heating the object. One such application is in the emerging field of medical hyperthermia, where tumors and cancerous tissue within a human body are heated by an external source as part of a program of medical treatment. For such treatment, the tumor is raised to a pre-determined elevated temperature and maintained there for a pre-determined period of time by directing electromagnetic radiation, in either the radio frequency or microwave spectrum, and/or ultrasonic energy from outside the body into the tumor. Each type of heating energy has advantages over the other for certain specific applications. Ultrasonic waves can be better focused and, because they are less strongly absorbed by tissue, are preferred for heating deep within the body. However, ultrasonic energy has disadvantages that include non-transmission through air or gas in a body cavity and high absorption by bone, resulting in electromagnetic energy being preferred when such body regions are involved.

In order to assure that the material being heated by either type of energy is maintained at the desired temperature, a non-perturbing temperature sensor is implanted in the tissue. In the case of cancer treatment of a human patient, such a sensor may be surgically implanted in the region to be heated prior to beginning the heating. Very small thermocouples and thermistors are traditionally used with either ultrasonic energy or electromagnetic radiation heating. More recently, fiberoptic temperature sensors have been employed to measure the temperature of materials heated by electromagnetic radiation. A significant advantage of the newer optical sensors is that they do not contain electrically conducting materials, thereby eliminating noise pickup and artifactual heating of the sensor that can result from the use of thermocouples and thermistors, as the result of electrical currents induced by the electromagnetic energy field. Also, the fiberoptic probes do not alter the incident heating field. Likewise, they do not conduct heat as strongly as do metallic wires or needles. As a result, measurements are more accurate in an environment having strong thermal gradients. For these reasons, significant sources of error in temperature measurements in an electromagnetic environment are eliminated.

Since the problem of induced currents does not exist with ultrasonic heating, however, thermocouples have until recently remained the technique of choice. Recently, however, it has been recognized that thermocouples also have problems in ultrasonic heating fields. Because of the acoustic mismatch, the thermocouple, unless extremely small, is driven relative to the tissue by the acoustic waves producing frictional or viscous heating. When plastic insulation is added or plastic catheters are used with thermocouples, absorptive heating is also observed. Finally, the thermo conduction of the metal leads can also produce errors in strong thermal gradients as noted above. Thus a better solution than thermocouples is also needed for ultrasonic heating fields. The fiberoptic sensors commonly used with electromagnetic heating contain plastics and therefore exhibit significant levels of absorption of ultrasonic energy. This causes an undesired measurement artifact from direct heating of the temperature sensor. Such artifacts are shown quantitatively in a poster paper entitled "Ultrasound-Immune Fiberoptic Thermometry Probe" that was given by applicants herein and others at the Annual Meeting of the Radiation Research Society, May 5–9, 1985. A solution suggested by this paper and related U.S. Pat. No. 4,626,110—Wickersheim and Sun (1986) is to select the materials and dimensions of the probe to minimize acoustic absorption, thermal conductivity and mismatch of acoustic impedance with the surrounding tissue. In order to minimize acoustic absorption, the fiber in the probe is selected to be quartz or glass because of its hardness.

It is a primary object of the temperature invention to provide an optical fiber temperature measurement sensor for use in an ultrasonic energy field that is a further improvement over that suggested by this poster paper and patent.

It is also an object of the present invention to provide an optical fiber temperature sensing probe that may be used with a variety of specific types of heating energy fields without itself introducing excessive errors.

SUMMARY OF THE INVENTION

These and additional objects are accomplished by the various aspects of the present invention, wherein, briefly, according to one aspect, an optical temperature sensor is formed at an end of an optical fiber by positioning a very small volume of temperature sensitive luminescent material at a distance from the fiber end, but in optical communication with it, the sensor being supported by a segment of optically clear but essentially incompressible material. As a result, the luminescent material is isolated from erroneous temperature artifacts produced within the fiber itself that are unrelated to the temperature of the material in which the probe is implanted. This allows, for example, inexpensive, non-brittle plastic fibers to be utilized for the probe. The fibers need not be made of silica, quartz, or other hard material in order to reduce the temperature artifacts to acceptable levels, but can be if there are other reasons to do so. This design thus allows the choice of whatever fiber type may be desired.

The support material is preferably conically or hemispherically shaped in a manner to provide sufficient optical coupling between the luminescent material and the optical fiber end. Efficient coupling allows the size of the luminescent sensor to be made very small, thus reducing temperature artifacts that might result from the sensor itself.

According to another aspect of the present invention, it has been found that the luminescent sensor may be attached directly to the end of a plastic fiber, without an isolating support therebetween, if the fiber is made small enough with respect to the wavelength of ultrasound in the medium in which the sensor is immersed. A total fiber diameter of less than about one-quarter wavelength has this advantage; or, more precisely, a diameter less than about the ultrasound wavelength divided by the mathematical constant pi. However, where larger fibers are desired to be used, use of the isolating sensor support described above with respect to the first aspect of the invention substantially eleminates the artifacts caused by it.

According to yet another aspect of the present invention, a plastic fiber having a diameter much larger than this threshold may be utilized without a separate isolating support attached to its end if it is tapered, over a sufficient distance, to a luminescent sensor carrying tip that is less in size than this threshold.

Each of these probe structures is also useful in an electromagnetic radiation field, since no electrically conducting materials are used, thereby making it possible to use a single sensor implantation for simultaneous or successive heatings by ultrasonic and/or electromagnetic techniques.

Additional objects, features and advantages of the various aspects of the present invention will become apparent from the following description of its preferred embodiments, which description should be taken in conjunction with the accompanying drawings.

BRIEF DESCRIPTION OF THE DRAWINGS

FIG. 1 schematically illustrates a typical heating and temperature measurement system in which the various temperature sensing probe embodiments of the present invention may be used;

FIG. 2 is a cross-sectional view of one embodiment of a temperature sensing probe according to a first aspect of the present invention;

FIG. 3 is a cross-sectional view of another embodiment of a temperature sensing probe according to the first aspect of the present invention;

FIG. 4 is a cross-sectional view of an embodiment of a temperature sensing probe according to another aspect of the present invention; and FIG. 5 is a cross-sectional view of an embodiment of a temperature sensing probe according yet another aspect of the present invention.

DESCRIPTION OF THE PREFERRED EMBODIMENTS

Referring to FIG. 1, an example is given of an environment in which the improved temperature sensing probes of the present invention are useful. A length of an optical fiber transmission medium 11, including one or a plurality of optical fibers, extends between an object 13, whose temperature is to be measured, and an instrument 17 that detects optical signals and provides such a measurement. A temperature sensor 15 is located at or near an end of the fiber transmission medium 11 and in optical communication therewith. In the embodiments illustrated, the sensor 15 is physically attached to the end of the fiber medium 11. The sensor 15 has some temperature dependent optical characteristic that is detected and measured by the instrument 17. The sensor 15 and a portion of that end of the fiber medium 11 are implanted or immersed in the medium or object 15 in order to measure its internal temperature. The medium or object 13 is heated by either an ultrasonic compressional wave energy source 19 or an electromagnetic radiation souce 21, or both at the same or successive times.

The improved temperature sensing devices and techniques of the present invention are not dependent upon the particular type of sensor 15 that is employed. Any one of many optical temperature sensors known in the art may be used if its dimensions can be made small enough. One class of such sensors utilizes a luminescent material. It is excited to luminescence by excitation radiation being directed down the fiber and temperature dependent luminescence is thus passed back through the fiber to the measuring instrument. The following two patents describe such a system which measures temperature dependent luminescence intensity: U.S. Pat. Nos. 4,448,547—Wickersheim (1984), and 4,376,890—Engstrom et al. (1983). The following two patents describe a system which measures the temperature-dependent decay time of luminescence: U.S. Pat. Nos. 4,245,507—Samulski (1981), and 4,223,226—Quick et al. (1980). Other types of devices rely upon temperature dependent absorption, reflectance or polarization, as exemplified, respectively, by the following patents: U.S. Pat. Nos. 4,136,566—Christensen (1979), 4,016,761—Rozzell (1977), and 4,140,393—Cetas (1979).

Regardless of the particular optical temperature sensing technique utilized, the present invention contemplates a physical structure of a temperature probe that is particularly useful in ultrasonic fields to make temperature measurements with high accuracy, as well as similarly being useful in electromagnetic radiation heating fields with similar accuracy. Such a structure is of great advantage in human hyperthermia where heating of internal body tissue or tumors may be accomplished by either form of radiation, and in some cases both at the same time. A treating physician may not know in advance of implanting the temperature sensing probes whether it is best to perform the heating by use of ultrasound or electromagnetic radiation. This may only be determined after a few temperature readings are taken using one type of heating or the other. A very ill patient may not be able to tolerate removal of one type of temperature probe and a subsequent implantation of another type when the type of heating radiation is changed. Yet, that is the current practice, since available radio frequency or microwave-immune sensors are perturbed by an ultrasound field. This is because of the absorption of ultrasound by the probe materials, including catheters through which they are frequently inserted, as well as viscous heating resulting from the acoustic mixmatch of the probe materials with the tissue.

Referring to FIG. 2, an embodiment of a temperature probe according to the present invention is described. The optical fiber 11 (FIG. 1) can be the inexpensive, non-brittle type of plastic fiber, this type having a plastic core 23 in a cylindrical shape and a plastic cladding 25 surrounding the core. A dome shaped piece of substantially optically clear, but essentially incompressible, material is constructed at the end of the core 23. A temperature sensor 29 is positioned on an opposite side of the material piece 27 in a position to be in optical communication with the fiber end. In the example being described, the sensor 29 is a luminescent material that is dispersed in an optically clear binder.

Because of temperature artifacts caused by the use of a plastic fiber in an ultrasound field, the element 27 serves to isolate the sensor layer 29 from transfer of heat by conduction from the core 23 and the cladding 25. The element 27 is made of material having a high degree of thermal insulation and is dimensioned so that the sensor 29 is separated an appropriate distance "a" from the fiber end to assure very low thermal transfer between the two. Further, so that the element 27 does not itself heat up by absorbing ultrasound, it is made to be incompressible. The degree of hardness of the elements 27 is selected to be much greater than that of the plastic fiber core 23 or cladding 25, in order to result in a probe that is affected by artifacts less than if the sensor 29 is attached directly to the end of the core 23 as in the case of usual probe structures. Also, so that the small quantity of binder used in the sensor layer 29 is not heated directly by absorptive of ultrasound, the layer is made to be hard, thin and smaller than the cross-sectional dimensions of the core 23, shown to have a diameter "d". The sensor 29 must be made large enough, however, to generate a temperature dependent optical signal with enough intensity to be detected by the instrument 17. The hemispherical shape of the element 27 acts to optically couple efficiently the available luminescence from the sensor 29 into the fiber core 23, thereby allowing the sensor to be very small.

The isolation element 27 can be made of a glass by being formed into a hemisphere shape and then attached to the end of the fiber core 23 by an adhesive. It is ususally more convenient, however, because of the extremely small size of the fiber in cross-section, to form the element 27 directly on the end of the fiber with a liquid polymeric material such as a hard epoxy. In this case, the fiber end is first dipped into the polymeric material and then adhering epoxy is cured by heating. The hard dome shaped element 27 results. The sensor layer 29 is then applied to the hardened element.

As a specific example of an implementation of the FIG. 2 sensor, the fiber is made of PMMA plastic and is chosen to have a diameter D at the outside of the cladding 25 that is about 250 microns. An advantage of plastic fibers over silica fibers, in addition to reduced cost and better mechanical strength, is that the plastic makes a better match acoustically to tissue than does silica. The sensor 29 itself has a diameter d of about 50 microns. The dimension a need not be very large, a distance of about 3-5 mils being satisfactory.

The embodiment of FIG. 3 is quite similar to that of FIG. 2, common elements being given the same reference number with a prime (') added. The primary difference is that the element 27' is elongated or conically shaped. This increases the distance a' between the fiber end and the sensor layer 29' to further thermally isolate the sensor 29' from the fiber. The structure of FIG. 3 otherwise has the same advantages as described above for the structure of FIG. 2.

Undesired temperature artifacts are generated in an optical temperature probe in an ultrasound field when its diameter or other cross-sectional dimension is large enough with respect to the length of the ultrasonic waves that compressional heating of the probe occurs. Additionally, frictional (viscous) heating results from accoustical incompatibility between the probe and its surroundings. The probe structures of FIGS. 2 and 3 allow a plastic fiber to be used even though it has a diameter large enough to be heated by the acoustic field. The isolation elements 27 and 27', respectively, effectively prevent that undesired heating from reaching the sensor 29 or 29'.

Commonly used ultrasonic heating frequencies in human hyperthermia extend from 300 KHz. to approximately 6 MHz., a range of from about 1 MHz. to 2 MHz. being most prevalent. The particular frequency chosen by a treating physician depends primarily upon the anatomical location of the tumor in the patient and the depth and nature of the volume to be heated. Most commonly used frequencies are 1 and 2 MHz., having a wavelength of approximately 1.5 and 0.75 mm, respectively, in human tissue.

It has been found as part of this invention that a sensor may be formed directly on the end of a plastic fiber, without suffering the effects of the compressional artifact, if the fiber is made to be less than about 0.25 the wavelength of ultrasound in the surrounding media. Stated more accurately from a theoretical point of view, it should be satisfactory if the fiber diameter is less than the ultrasound wavelength divided by the mathematical constant pi, or about 0.32 the wavelength. Such a structure is shown in FIG. 4. No isolating sensor support structure is required at the end of the fiber. Example dimensions of the probe structure of FIG. 4 for use in the common 1-2 MHz. range, or lower, is a fiber diameter D" of about 180 microns. The fiber has no jacket or buffer.

As another embodiment of the present invention, FIG. 5 shows a fiber having a diameter D''' in excess of the threshold where compressional heating occurs. But that heating is isolated from the luminescent sensor 29''' by a tapered portion of the fiber, much of which, for a length adjacent the sensor 29''', has a diameter less than that threshold. Example dimensions are a fiber diameter D'''of about 250 microns and a length a''' of about two centimeters.

The examples of the Figures show luminescent temperature sensing probes formed of a single fiber, but, as the above-referenced patents show, some optical sensing techniques may make it desirable or a requirement to employ two or more independent fibers terminating in a single sensor. The structures described can be modified to meet that requirement. Further, it may be desirable to provide a linear array of multiple sensors at ends of independent fibers.

Although the various aspects of the present invention have been described with respect to a preferred embodiment thereof, it will be understood that the invention is entitled to protection within the full scope of the appended claims.

It is claimed:

1. A method of monitoring the temperature of a volume of material that is being heated by absorption of ultrasonic energy directed into said volume of material from its outside, comprising the steps of:
   implanting within said material one end of an optical fiber transmission medium which forms an optical temperature probe, said probe being characterized by having (1) a segment of substantially optically transparent and incompressible material attached to said one end of the optical fiber transmission medium, and (2) an optical temperature sensor attached to a surface of said material piece a distance removed from said one fiber end and in optical communication therewith through said material piece, and
   monitoring the temperature of said sensor by optical communication through another end of said optical fiber transmission medium to said optical temperature sensor.

2. The method according to claim 1 wherein the step of implanting a probe includes the step of selecting an optical fiber transmission medium that is characterized by having a core and surrounding cladding, and said material segment is further characterized by being significantly harder than said core or cladding.

3. The method according to claim 2 wherein the step of implanting a probe includes the step of selecting an optical fiber transmission medium that is further characterized by its core and cladding being made of plastic material.

4. The method according to claim 1 which comprises an additional step of irradiating said volume of material with electromagnetic radiation, thereby heating said volume both ultrasonically and electromagnetically, whereby the step of monitoring the temperature of said volume detects heating from both the ultrasonic and electromagnetic sources.

5. The method according to claim 1 wherein said volume of material is within a human body.

6. A temperature sensing probe especially adapted for being implanted into a volume of material that is being heated by absorption of ultrasonic energy directed into said volume from its outside, comprising:
   a length of optical fiber transmission medium that includes both a core and surrounding cladding made of plastic material,
   a substantially optically transparent element affixed to an end of said fiber medium and having a degree of hardness significantly greater than that of said fiber medium core or cladding material, and
   an optical temperature sensor held by said element in a position removed a distance from said fiber medium end but in optical communication therewith through said element.

7. The probe according to claim 6 wherein said element is additionally characterized by being substantially non-conductive electrically.

8. The probe according to claim 6 wherein said element includes a hemispherically shaped piece.

9. The probe according to claim 6 wherein said element includes a conically shaped piece.

10. The probe according to claim 6 wherein said optical temperature sensor has cross-sectional dimensions that are smaller than that of said fiber medium core.

11. The probe according to claim 6 wherein said optical temperature sensor includes a luminescent material.

12. A temperature sensing probe especially adapted for being transplanted into a volume of material that is being heated by absorption of ultrasonic energy directed into said volume from its outside, comprising:
   a length of optical fiber transmission medium that includes both a core and surrounding cladding made of plastic material,
   said fiber medium being tapered to a minimum dimension at one end thereof, and
   an optical temperature sensor carried by said minimum dimension end of said fiber medium.

13. A method of monitoring the temperature of a volume of material that is being heated by absorption of ultrasonic energy directed into said volume of material from its outside, comprising the steps of:
   implanting within said material one end of an optical fiber transmission medium which forms an optical temperature probe, said probe being characterized by (1) a tapered conical shape having a minimum dimension at an extreme of said one end, and (2) an optical temperature sensor attached to a surface of said fiber medium at said minimum dimension end and in optical communication therewith, and
   monitoring the temperature of said sensor by optical communication through another end of said optical fiber transmission medium to said optical temperature sensor.

14. The method according to claim 13 wherein the step of implanting a probe includes the step of selecting an optical fiber transmission medium that is further characterized by having core and cladding portions made of plastic material.

15. The method according to claim 14 wherein said volume of material is within a human body.

16. A method of monitoring the temperature of a volume of material that is being heated by absorption of ultrasonic energy directed into said volume of material from its outside, comprising the steps of:
   implanting within said material one end of an optical fiber transmission medium which forms an optical temperature probe, said optical fiber transmission medium having core and cladding portions made of plastic material and an outside diameter that is less than a wavelength of ultrasonic energy in said material divided by the mathematical constant pi, said probe including an optical temperature sensor attached directly to the fiber core at its said one end in a manner to be in optical communication therewith, and
   monitoring the temperature of said sensor by optical communication through another end of said optical fiber transmission medium to said optical temperature sensor.

17. The method according to claim 16 wherein said volume of material is within a human body

* * * * *

UNITED STATES PATENT AND TRADEMARK OFFICE
CERTIFICATE OF CORRECTION

PATENT NO. : 4,785,824
DATED : November 22, 1988
INVENTOR(S) : Wickersheim et al.

It is certified that error appears in the above-identified patent and that said Letters Patent is hereby corrected as shown below:

col. 7, line 50, "transplanted" should be --implanted--

Signed and Sealed this

Eleventh Day of April, 1989

Attest:

DONALD J. QUIGG

*Attesting Officer*  *Commissioner of Patents and Trademarks*